(12) United States Patent
Shahriari

(10) Patent No.: US 7,862,770 B2
(45) Date of Patent: Jan. 4, 2011

(54) PATCHES FOR NON-INTRUSIVE MONITORING OF OXYGEN IN PACKAGES

(75) Inventor: Mahmoud R. Shahriari, Palm Harbor, FL (US)

(73) Assignee: Ocean Optics, Inc., Dunedin, FL (US)

(*) Notice: Subject to any disclaimer, the term of this patent is extended or adjusted under 35 U.S.C. 154(b) by 302 days.

(21) Appl. No.: 12/220,046

(22) Filed: Jul. 21, 2008

(65) Prior Publication Data

US 2009/0028756 A1    Jan. 29, 2009

Related U.S. Application Data

(60) Provisional application No. 60/962,396, filed on Jul. 27, 2007.

(51) Int. Cl.
*G01N 21/00* (2006.01)
(52) U.S. Cl. .................................................. 422/58
(58) Field of Classification Search ............... 422/58
See application file for complete search history.

(56) References Cited

U.S. PATENT DOCUMENTS 6,689,438 B2 * 2/2004 Kennedy et al. ............ 428/36.6
2006/0257094 A1 * 11/2006 McEvoy et al. ............. 385/147

OTHER PUBLICATIONS

O'Mahony F.C.; O'Riordan, T.C.; Papkovskaia, N.; Kerry, J.P.; Papkovsky, D.B. "Non-destructive assessment of oxygen levels in industrial modified atmosphere packaged cheddar cheese." Food Control, 2006, 17, pp. 286-292.*
Basu, B. "Optical oxygen sensing based on luminescence quenching of platinum porphyrin dyes doped in ormosil coatings." Sensors and Actuators B, 2006, 123, pp. 568-577.*
McDonagh, C.; MacCraith, B.D.; McEnvoy, A.K. "Tailoring of Sol-Gel Films for Optical Sensing of Oxygen in Gas and Aqueous Phase." Anal. chem. 1998, 70, pp. 40-50.*
Papkovsky, D.B."Sensors for Food Safety and Security." Optical Chemical Sensors. Springer Netherlands, 2006, pp. 501-514.*
Shahriai, M.R.; Ding, J.Y.; Tong, J.; Sigel, Jr., G.H. "Sol-Gel Coating Based Figer Optic O2/DO Sensor." Proc. SPIE, 1993, vol. 2068, pp. 224-240.*
Okui, T; Saito, Y.; Okubo, T.; Sadakata, M. "Gas Permeation of Porous Organic/Inorganic Hybrid Membranes." Journal of Sol-Gel Science and Technology, 1995, 5, pp. 127-134.*

* cited by examiner

*Primary Examiner*—Walter D Griffin
*Assistant Examiner*—Bobby Ramdhanie
(74) *Attorney, Agent, or Firm*—Dennis L. Cook, Esq.

(57) ABSTRACT

This disclosure describes an Oxygen sensing patch that can be attached to the interior surface of packages for oxygen interrogation inside the package. The Oxygen sensing patch is integrated into the inside of the package during the packaging manufacturing process and, when used with a blue LED and fluorometer, will quantitatively report the amount of oxygen in the package. The Oxygen sensing patch is suitable for measuring oxygen in gas, such as headspace applications, and in liquid. Oxygen is sensed by measuring the phase shift of fluorescence of the fluorophore immobilized in the Oxygen sensing patch. The patch can be non-intrusively interrogated by a light source. The interrogation can be done using a phase fluorometer where oxygen level is desired, or inspected visually for color change using a hand held blue LED.

4 Claims, 2 Drawing Sheets

FIGURE 1

| Specification | Dissolved Oxygen in H20 | Oxygen Gas (at 1 atmosphere) |
|---|---|---|
| Sensor mechanism: | Phase shift due to change in partial pressure of O2 | |
| Dynamic range: | 0-40.7 ppm<br>0-760 mm Hg partial pressure | 0-100% (mole percent)<br>0-760 mm Hg partial pressure |
| Response time (standard): | ~ 1 second | |
| Response time (w/overcoat): | 30-50 seconds | 20-30 seconds |
| Temperature | Temperature sensor and software-supported compensation | |
| Temperature range: | 0° C to 50°C | |
| Chemical compatibility of coating: | • Unaffected by pH change or salinity<br>• Not recommended with strong bases (pH>10), styrene, ethanol, liquid acetone, acetonitrile, HF and BTX solvents | |
| Resolution: | 0.02 ppm at Room Temperature | 0.05% (0.04 mmHg) at Room Temperature |
| Calibration: | • Standard 2-point calibration (linear fit)<br>• Multipoint calibration (second-order polynomial fit) for improved accuracy and broad dynamic range applications<br>• Single-temperature, single-point calibration using factory-calibrated FOXY patches | |
| Accuracy: Accuracy (0-20% O2, 0-50 C) | 5% of reading within 10°C differential (using 2nd order polynomial fit to multipoint calibration) | |
| Lowest detectable limit | 0.02 PPM | 0.05% (0.4 mm Hg) |
| Stability: | Drift <0.01 ppm per HR | Drift ~ 0.02% O2 per HR |
| Patch reconditioning: | N/A | N/A |
| Temperature recalibration: | N/A | N/A |
| Storage conditions: | No specific requirements | No specific requirements |
| Cleaning: | 10% hypochlorite detergent for over coated probes | |
| Sterilization: | Gamma radiation | |
| Probe lifetime: | One year, may vary depending on usage and application. | |

PATCHES FOR NON-INTRUSIVE MONITORING OF OXYGEN IN PACKAGES

CROSS-REFERENCE TO RELATED APPLICATION

The present application claims the benefit of previously filed co-pending Provisional Patent Application, Ser. No. 60/962,396.

FIELD OF THE INVENTION

This invention belongs to the field of optical sensors and/or monitors based on absorption and/or fluorescence detection. It is a new process for manufacturing an oxygen sensitive patch (label) to hold or encapsulate sensing molecules. The patch adhesive and support material can be tailored for direct food contact compatibility as well as medical applications.

BRIEF SUMMARY OF THE INVENTION

The patch of this invention is designed for a wide range of applications. The patch can be attached to the interior surface of packages for oxygen interrogation inside the package. The patch then is non-intrusively interrogated by a light source. The interrogation can be done using a phase fluorometer where oxygen level is desired, or inspected visually for color change using a hand held blue LED. Some of the immediate applications for the Oxygen sensing patch are:

Medical and Biological
1. Point of care analysis (for example, disposable oxygen attachments for ventilators used during anesthesia operation)
2. Blood bags
3. Respiration
4. Bioprocess control
5. Cell culture monitoring
6. Packaging for surgical tools
Pharmaceutical
7. Pharmaceutical packaging
8. Pills blister packages
Food Packaging
9. Modified atmospheric packaging For a fuller understanding of the nature and objects of the invention, reference should be made to the following detailed description taken in connection with the accompanying drawings.

BRIEF DESCRIPTION OF THE DRAWINGS

For a fuller understanding of the nature and objects of the invention, reference should be made to the following detailed description, taken in connection with the accompanying drawings, in which:

FIG. 1 is a table of specifications for the Oxygen detecting patch.

DESCRIPTION OF THE PREFERRED EMBODIMENT

Figure 2:
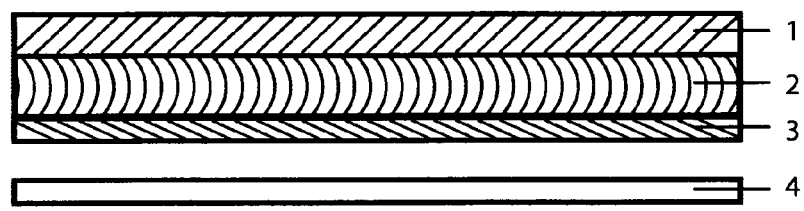
FIG. 2 is a side view drawing showing the Oxygen detecting patch.

The Oxygen sensing patch of this invention is a new oxygen sensing product designed specifically to measure oxygen in packaging. The Oxygen sensing patch is integrated into the inside of the package during the packaging manufacturing process and, when used with a blue LED and fluorometer, will quantitatively report the amount of oxygen in the package. The Oxygen sensing patch is suitable for measuring oxygen in gas, such as headspace applications, and in liquid. Oxygen is sensed by measuring the phase shift of fluorescence of the fluorophore immobilized in the Oxygen sensing patch. The oxygen sensing measurement can be taken at many different stages of the product's lifetime: when the product passes through a manufacturing stream; when the product is about to ship to a customer; while the product is being stored in inventory; and, before the product is about to be consumed by the end-user.

More specifically the Oxygen sensing patch uses the fluorescence quenching properties of a ruthenium or porphyrin complex to measure the partial pressure of dissolved or gaseous oxygen. The Oxygen sensing patch consists of one of three sensor coating formulations trapped in a sol-gel matrix, immobilized, and protected from the contents in the package. An optical probe is then pointed at the part of the package where the Oxygen sensing patch has been applied. The optical probe is connected to a blue LED and Fluorometer. The blue LED sends excitation light via an optical probe. The light from the blue LED passes over the Oxygen sensing patch and excites the sensor coating formulation. The excited Oxygen sensing patch then fluoresces. If the Oxygen sensing patch encounters an oxygen molecule, the excess energy is transferred to the oxygen molecule in a non-radiative transfer, decreasing or quenching the fluorescence signal. The degree of quenching correlates to the partial pressure of oxygen in the sol-gel matrix, which is in dynamic equilibrium with oxygen in the sample. If oxygen is present, a user can visually observe the Oxygen sensing patch turning pink. The fluorescence is collected by the optical probe and transmitted to the Fluorometer. The fluorescence phase is measured and related to the partial pressure of oxygen through the Stern-Volmer equation.

The novelty of this invention relates to the use of Ocean Optics' sol gel as oxygen sensitive coatings on flexible patches for new applications. The sol gel process, called ormosil, (organically modified silica), enables the new product to be used an in environment where no other presently available sensors can operate. An Ocean Optics' FOSPOR coating (pt. porphyrine doped sol gel) is designed to monitor ppb levels of oxygen in vacuum environments; Ocean Optics' HIOXY coating is designed to monitor oxygen in hydrocarbon based environments such as fuels, solvents, oil, alcoholic beverages, etc. The current conventional sol-gel mediums used in optical sensors are not suitable for packages containing volatiles, oils and other hydrocarbon derived products.

This preferred embodiment of this new invention involves the following steps. (1) Addition of sol gel precursor MTMS (methyltrimethoxysilane, MTMS)+fluorinated sol gel precursor [(3,3,3-trifluoropropyl)triethoxysilane]+water+ethyl alcohol together. (2) Doping the multi-component sol-gel with tris-(4,7-diphenyl-1,10-phenanthroline) ruthenium(II) chloride, (3) coating the doped sol gel on self adhesive acrylate patches by spin coating, (3) thermal and optical curing of the coating. Fluorinated sol gel provides resistance toward hydrocarbons due to its oleophobic properties, and MTMS forms a backbone glass structure with mechanical integrity and crack free coating. Once cured, the patches are attached to the inner surface of a package to be monitored. The oxygen level is then monitored either by shining blue light on the patch and visually inspecting the color of the patch (patch is orange when oxygen level is high and reddish when oxygen level is low) or by inspecting the excited state lifetime of luminescence of the batch by using a phase fluorometer. A phase fluorometer is used for excitation and emission collection of light. The excitation light transmission to the patch, and capture of the reflected emission from the patch, is performed using a bifurcated fiber optic bundle.

As shown in FIG. 2 The patch is a self-adhesive acrylic support (2) coated with oxygen sensitive sol gel (1). The patch is 3.0 mil (76 micron) self-adhesive poly acrylate (2) with 20 micron high track acrylic adhesive (3) and 38 micron polyester liner (4). The sensor coating (1) is applied on the non-adhesive side of patches. The patch diameter is 8 mm but it can be custom made for other diameters. The patch material is currently poly acrylate. Other polymers can be used as support for specific applications. The patches have been tested in Ocean Optics' environmental chamber where they have been exposed to a matrix of oxygen gas mixes and temperatures while the excited state lifetime of patch luminescence was collected using a phase fluorometer. The initial specification for preferred embodiment patches are shown below in the table of FIG. 1.

Since certain changes may be made in the above described Oxygen sensing patch without departing from the scope of the invention herein involved, it is intended that all matter contained in the description thereof or shown in the accompanying figures shall be interpreted as illustrative and not in a limiting sense.

What is claimed is:

1. An Oxygen sensing patch using fluorescence quenching for sensing Oxygen in liquids or gases that can be used inside an enclosed area or container such as product packaging comprising: a flexible patch with adhesive on one side such that said flexible patch can be placed and held on a surface inside an enclosed area or container containing a gas or liquid to be measured for Oxygen content wherein said flexible patch is a poly acrylate consisting of 3.0 mil (76 micron) self-adhesive poly acrylate with 20 micron high track acrylic adhesive and 38 micron polyester liner; a sol gel matrix of organically modified silica that is made from a mixture comprising sol gel precursors, that is doped with a ruthenium or porphyrin complex and coated on the side of said flexible patch without the adhesive and then cured; and, said enclosed area or container having a clear area or window such that blue light can be shown through said clear area or window onto said flexible patch and fluorescence from said ruthenium or porphyrin complex contained in said sol gel matrix can be detected through said clear area or window to measure the partial pressure of dissolved or gaseous Oxygen.

2. The Oxygen sensing patch of claim 1 wherein said sol gel mixture prior to being doped and cured, comprises a mixture of sol gel precursor MTMS (methyltrimethoxysilane, MTMS), fluorinated sol gel precursor [(3,3,3-trifluoropropyl)triethoxysilane], water, and ethyl alcohol.

3. The Oxygen sensing patch of claim 1 wherein said ruthenium complex consists of tris-(4,7-diphenyl-1,10-phenanthroline) ruthenium(II) chloride.

4. The Oxygen sensing patch of claim 1 wherein said sol gel matrix that is doped with a ruthenium or porphyrin complex is coated on said flexible patch by spin coating and is then thermally and optically cured.

* * * * *